United States Patent [19]

Malinge et al.

[11] Patent Number: 4,645,821
[45] Date of Patent: Feb. 24, 1987

[54] PRECURSOR OF COPOLYPHTHALOCYANINE-IMIDE LATTICE, PREPARATION, AND THE RESULTANT LATTICE

[75] Inventors: Jean Malinge, Givors; Guy Rabilloud, Grenoble; Bernard Sillion, Lyons, all of France

[73] Assignee: Centre d'Etude des Materiaux Organiques pour Technologies Avancees, Vernaison, France

[21] Appl. No.: 758,949

[22] Filed: Jul. 25, 1985

[30] Foreign Application Priority Data

Jul. 25, 1984 [FR] France ................................ 84 11841

[51] Int. Cl.$^4$ .............................................. C08G 73/06
[52] U.S. Cl. ...................................... 528/331; 528/170; 528/183; 528/184; 528/220; 528/228; 528/229; 528/322; 528/327; 528/329.1; 528/353; 528/362
[58] Field of Search ...................... 528/331, 329.1, 184, 528/362, 327, 220, 228, 229, 183, 170, 322, 353

[56] References Cited

U.S. PATENT DOCUMENTS 3,993,631  11/1976  Griffith et al. ................. 528/331

*Primary Examiner*—Harold D. Anderson
*Attorney, Agent, or Firm*—Millen & White

[57] ABSTRACT

Aromatic polyimide compositions, precursors of copolyphthalocyanine-imides, their manufacturing process and the resultant copolyphthalocyanine-imides, are described.

These compositions may result for the reaction of 80°-300° C. of an aromatic tetra acid, diester-diacid, tetraester or dianhydride compound of formula:

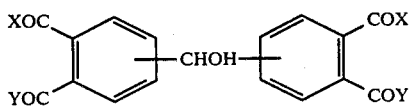

with an aromatic amino-dinitrile

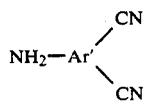

and optionally an aromatic diamine $NH_2-Ar-NH_2$.

A subsequent heating at 200°-300° C. provides, by cross-linking, copolyphthalocyanine-imides, which are hardened resins, stable at 250°-300° C. in continuous use.

20 Claims, No Drawings

PRECURSOR OF COPOLYPHTHALOCYANINE-IMIDE LATTICE, PREPARATION, AND THE RESULTANT LATTICE

An object of the present invention is to provide new thermosetting imide oligomeric compositions of high solubility in organic solvents. It concerns more particularly oligomer formed of imide rings linked together through benzhydrol groups and ending with ortho-dinitrile groups.

The invention concerns a process for cyano-addition of ortho-dinitrile groups giving polyphthalocyanines by oxidation-reduction initiated with benzhydrol groups.

The invention also concerns polyimide-copolyphthalocyanine lattices formed during cyano-addition reactions.

The soluble polyimide compositions, precursors of copolyphthalocyanine-imides, may be used as binding agents in the manufacture of composite materials, as adhesives, as insulating films and varnishes and as raw materials for manufacturing molded articles and cellular materials.

BACKGROUND OF THE INVENTION

Simple phthalocyanines are generally solid compounds of dark green color, having a high melting temperature and a very low solubility in organic solvents. It is hence very difficult to prepare polyphthalocyanines of high molecular weight or to use this type of polymer in their final cyclized form. On the contrary, the cyano-addition reactions may be used to cross-link monomers or easily melted and soluble oligomers, the cross-linking reactions being performed by mere heating at the moment of use of the products.

Such cyano-addition reactions have been disclosed with aromatic or arylaliphatic compounds containing amides, azomethines or ethers chainings (Walton and Griffith: Applied Polymer Symposium, 1975, 26, 429; Polymer Science and Technology, 1975, 9B, 665; ACS Division of Organic Coatings and Plastics Chemistry, 1978, 38, 596. Keller and coll., SAMPE Quaterly, July 1981, P.1). In these publications and in U.S. Pat. Nos. 4,056,560, 4,057,569, 4,102,873, 4,116,945, 4,136,107, 4,209,458, 4,223,123, 4,234,712 and 4,238,601, the formation of phthalocyanines is described as a very slow reaction which, in the absence of metal salts, may last several hours and sometimes several days at a temperature generally ranging from 200° to 300° C. Moreover, Marullo and Snow (ACS symposium series, vol. 195, 1982, p. 325) have shown that the selectivity of the reaction of phthalocyanine formation is very low and that the cross-linked lattice is in fact a complex mixture containing several types of hererocyclic systems. Finally, the thermal stability of the thermoset resins is limited by the nature of the starting molecules.

In order to increase the thermal stability of phthalocyanine resins, highly thermostable heterocyclic structures such as for example, aromatic imides, can be introduced in the macromolecular chain. But polyimides, even as oligomers of low molecular weight, have too high a melting temperature and too low a solubility to form good precursors of polyphthalocyanines.

SUMMARY OF THE INVENTION

It has now been discovered, and this is one of the objects of the invention, that oligomers containing aromatic imide rings linked by benzhydrol moieties constitute noteworthy compositions for the manufacture of easily melted, soluble resins which can set, when heated, by subsequent cyano-addition reactions. The first advantage of these compositions is a very high solubility in many polar organic solvents, thus making it possible to prepare solutions of high solids content.

The second advantage is the consequence of a remarkable stabilit of those type of polyimides which, after cyano-addition reaction, give resins which are adapted to a continuous use at a temperature ranging from 250° to 300° C. Finally, and this is one of the most interesting results obtained with these compositions, their gelation time, at the moment of thermal cross-linking, is much shorter than that which is generally described for other polyphthalocyanines. This quite surprising behaviour, which is one of the objects of the invention, results from an intramolecular oxidation-reduction phenomenon occurring between the benzhydrol group and the ortho-dinitrile groups, as shown in the comparative examples. This reaction results in a gelation time of only a few minutes at a temperature from 180° to 300° C. The manufacturing cycles in the press or in an autoclave are hence considerably shortened as compared with those of other polymers whose manufacture involves cyano-addition reactions.

The invention has more particularly for object polyimide resins compositions, precursors of copolyphthalocyanine-imide lattices, of the general formula:

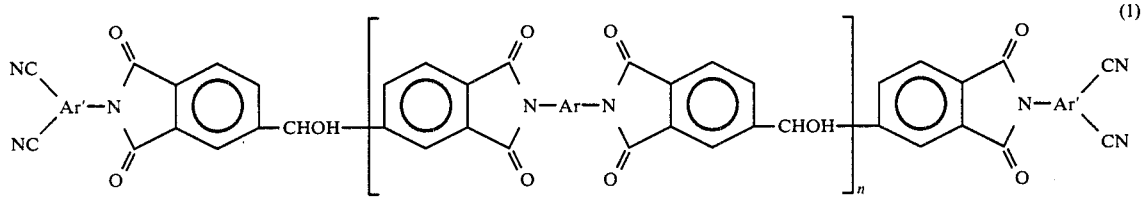

In these formulas, radical Ar is a divalent carbocyclic or heterocyclic aromatic radical, the two valencies of which are fixed on separate carbon atoms not in ortho position with respect to each other. Radical Ar may be formed of one ring or several rings which are then coupled or linked together, each ring being preferably formed of 5-7 atoms, a part of which may consist of oxygen, sulfur and/or nitrogen atoms.

When radical Ar comprises several interlinked rings, the linking elements are for example a single bond or one of the following atoms and groups: —O—; —S—; —SO—; —SO$_2$—; —CH$_2$—; CF$_2$—; —C(CH$_3$)$_2$—; —CO—; —CHOH—; —COO—; —CONH—.

The radical Ar' is a trivalent carbocyclic or heterocyclic aromatic radical whose three valencies are on separate carbon atoms two of them, which carry nitrile groups, being obligatorily in the ortho position with respect to each other. Radical Ar' may be formed of one ring or several coupled or interconnected rings, as above-defined for radical Ar.

n is a number whose value may range from 0 to 50 and which indicates the polycondensation degree. n cannot be directly determined but its average value can be deduced from the molar proportions of the reactants used to prepare the benzhydrolimide oligomer compositions. The determination of n is explained hereinafter with the technique of manufacturing the polyimide compositions. When n is zero, the obtained products conform with the general formula:

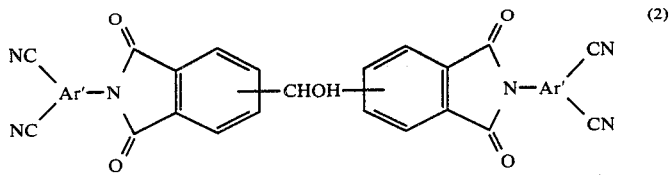

(2)

wherein Ar' has the same meaning as above.

Polyimide compositions of formula (1) may be prepared by reacting at least one aromatic compound (A) of the general formula

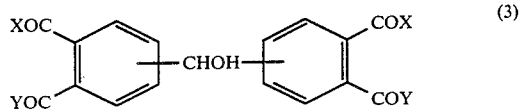

(3)

with at least one aromatic amino-dinitrile compound (C) of the general formula

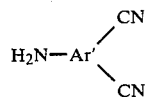

(4)

and optionally with at least one aromatic diamine (B) of the general formula $$H_2N-Ar-NH_2$$ (5)

In these formulas Ar and Ar' have the same meaning as above. X and Y, identical or different, are radicals which represent the nature of the reacting centers, which may be carboxylic acids, their esters or their anhydrides. When X and Y are hydroxyl radicals, compound (A) is 3, 3', 4, 4'-benzhydrol tetracarboxylic acid. The dianhydride of said acid conforms with formula (3) wherein X and Y are together an oxygen atom.

When X is a hydroxyl radical and Y an alkoxy radical, preferably containing 1–13 carbon atoms, the compound of formula (3) represents a bis-orthoacidester (or diester) of benzhydrol tetracarboxylic acid. Finally, when X and Y are both hydrocarbyloxy radicals, the product is an alkyl tetraester of said acid. The carbinol group which separates the two aromatic rings of benzhydrol is placed at the middle of said rings to indicate the posssible isomerisms for dissymmetric derivatives.

Convenient diamines according to this invention are: 1,3- and 1,4-diamino benzenes,3,3'- and 4,4'-diamino-diphenyl methanes, 3,3'- and 4,4'-diamino-diphenyl ethers, benzidine, 3,3'- and 4,4'-diamino-diphenyl sulfides, 3,3' and 4,4'diaminodiphenyl sulfones, 3,3'- and 4,4'-diamino benzophenones, 3,3'- and 4,4'-diamino-benzhydrols, 3,3'- and 4,4'-diaminobenzanilides, 3,3'- and 4,4'-diamino-phenyl benzoates, bis (4-amino phenyl) dimethyl silane, 2,4, (2,6) and 3,5 diaminopyridines, 3,3'-dimethoxy benzidine.

Examples of aromatic amino-dinitriles which can be used according to the invention are: 3 and 4-amino phthalonitriles, 4-para and meta-aminophenoxy)phthalonitriles, 4'- amino 3,4-dicyano biphenyl, 4'-amino-3,4 dicyano diphenyl methane, 3' and 4 -amino-3 4-dicyano benzophenones,3'- and 4'-amino3,4-dicyano benzhydrols.

Examples of 3, 3', 4,4'-benzhydrol tetracarboxylic acid derivatives which are convenient for the invention, are: the tetra-acid itself, its dianhydride, methyl, ethvl, isopropyl, butyl and 2-hydroxy-ethyl diesters, methyl and ethyl tetraesters.

Resins of the general formula (1) may be prepared in one or two steps depending on the introduction of the reactants simultaneously or twice. The total stoichiometry of the reaction is always the same since it consists of using in the condensation a number of amine groups, originating from the aromatic diamine and from the amino-dinitrile, which is substantially equal to the number of reacting groups of the compound of formula (3). More precisely, for one ortho-difunctional reacting center of the latter compound, preferably a total of 0.9 to 1.1 amine group is used. The best results are obtained with a proportion from 0.98 to 1.02 primary amine group.

As above stated, primary amine groups originate either in totality from aminodinitrile of formula (4), and the polycondensation degree n is then equal to zero, or partly from the aminodinitrile and partly from the one or more aromatic diamines of formula (5); the polycondensation degree being then greater than zero.

The respective proportions of the two amine compounds determine the polycondensation degree since the molecular weight of the polyimide resin composition higher as the molar ratio between compound (A) and the aromatic diamine becomes closer to 1.

In accordance with the expected uses, the number n may have a value within the range of 0 to 50 and preferably 0 to 20. This means that for 1 mole of compound (A), 0 to 0.98 and preferably 0 to 0.95 moles of aromatic diamine is used. Since initially two ortho-difunctional reacting centers are available per mole of compound (A), to which are opposed from 0 to 1.96 (preferably from 0 to 1.90) amine groups originating from the diamine, it is necessary, for restoring the stoichiometrical balance, to add respectively from 2 to 0.04 moles and preferably from 2 to 0.1 mole of amino-dinitrile.

The above indicated values are given as examples to show how the polycondensation degree of resins complying with general formula (1) can be linked to the relative proportions of the various reactants.

Resins of general formula (1) wherein n is different from zero may be prepared in two successive steps which can be performed in the same reactor. During the first step the aromatic diamine of formula (5) (or the mixture of aromatic diamines) is reacted with an excess of aromatic compound of formula (3) in an organic solvent, heated at a temperature sufficient for promoting the polycondensation reaction and the reaction of cyclization to imide of all the reacting antagonistic groups.

The resultant compositions at the end of the first step are formed of oligomers statistically ending with reacting groups of the compound used in excess. These benzhydrolimide oligomers may be represented by the general formula:

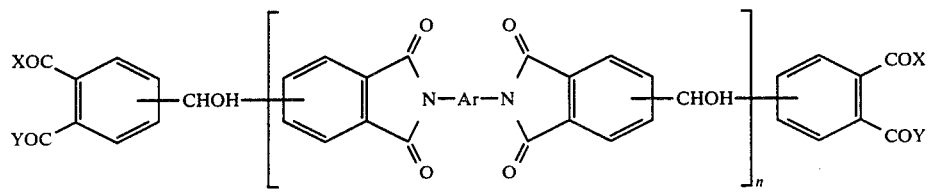

(6)

wherein Ar, X, Y and n have the same meaning as above. They generally have an average molecular weight from 800 to 25 000.

At the end of this first step, the amino-dinitrile of formula (4) is introduced in the reaction medium in a sufficient amount to bring at least one amine group to each ortho-difunctional reacting center of imide oligomers mixture of formula (6). The condensation reaction is then continued until practical disappearance of free amine groups in the reaction medium.

Resins of general formula (1) may also be prepared in a single step by admixing simultaneously three reactants (A), (B) and (C) in an organic solvent and by heating the mixture up to the completion of the polycondensation reaction. The proportions of each reactant are, as above indicated, calculated in accordance with the desired average molecular weight.

The polyimide compositions of low molecular weight of formula (2) are prepared by the same process, by reacting in an organic solvent a molar equivalent of aromatic compound of formula (3) with at least two equivalents of amino-dinitrile of formula (4).

Solvents which can be used for preparing the compositions according to the invention are polar organic compounds, i.e. containing one or more heteroatoms such as O, N, S, P, Cl, inert with respect to the monomers and polymers. Examples of such solvents are phenol, cresols, xylenols, chlorobenzene, dichlorobenzenes, ethyleneglycol and diethyleneglycol mono- and diethers, dimethylformamide, dimethylacetamide, hexamethylphosphotriamide, tetramethyl urea, dimethylsulfoxide, pyridine, quinoline, N-methylpyrrolidone, dioxane, tetrahydrofuran, tetramethylenesulfone.

These solvents may be used alone or as mixtures with each other or still as mixtures with other liquid organic compounds as aromatic hydrocarbons, alcohols, ketones, esters or halogenated compounds.

The initial concentration of the monomers in the reaction solvent is not critical but is generally from 20 to 80% by weight. At the end of the reaction, the concentration of resinous composition is adjusted to such a value that the solution has a dynamic viscosity well adapted to the considered use. In other terms, the final concentration depends on the molecular weight of the imide oligomers, on the nature of the one or more solvents and on the temperature. For certain applications where the polyimide resin must be used as solid or dissolved in another solvent than that used for preparing it, the product is precipitated in a liquid non-solvent compound. For sake of simplicity this precipitation is generally performed in water when the basic solvent is miscible therewith. Examples of other non-solvents are alcohols, ethyl ether and aliphatic hydrocarbons.

The temperature of the polycondensation reaction may vary within a wide range, from 80° to 300° C. Generally it is set at such a value that the reaction of the amine groups on the derivatives of benzhydroltetracarboxylic acid takes place at a reasonable rate. Depending on the solvent and the reactants, a temperature from 100° to 200° C. generally gives good results. Above 200° C., the formation of the cross-linked lattice may disturb the normal linear polycondensation cycle. The volatile products formed during the reaction may be kept in the medium but they are generally removed by distillation as they are formed, thereby controlling the progress of the reaction.

The formation of phthalocyanine lattices from resin precursors of the invention is achieved at the moment of use. The final properties of the thermoset resin strictly depend on the nature of the diamine and on the length of the polyimide chains between each ortho-dinitrile group.

Co-polyphthalocyanine-imide precursor resins of low molecular weight have a melting temperature generally from 150° to 300° C. Beyond a certain chain length, i.e. for a polycondensation degree of more than 7 or 8, the polyimide resins have a vitreous transition temperature ranging from 220° to 350° C., depending on the nature of the diamine.

The selection of the one or more polyimide resins compositions used for a determined application depends, on the one hand, on the desired properties and, on the other hand, on the technique of use imposed by the available type of equipment. As resins of different molecular weights are perfectly compatible with each other, it is possible to use mixtures in various proportions of easily melted resins of low molecular weight with resins of higher molecular weight.

At the time of use, thermosetting polyimide resins according to the invention are heated to a sufficient temperature to promote cyano-addition reactions of the ortho-dinitrile groups. The formation of phthalocyanine rings results in the formation of a green colour which becomes more and more dark as polymerization progresses. In infrared spectroscopy, the absorption bands of nitrile groups at 2230 cm$^{-1}$ progressively disappear.

With polyimide compositions of low molecular weight whose melting temperature ranges for example from 150° to 300° C., the cross-linking reactions are advantageously performed between 200° and 300° C. The viscosity of the melted mixture quickly increases and the gelation takes place after 5–15 minutes of heating. The polymerization then continues more slowly in solid phase until substantially all the nitrile groups have reacted. Being assumed that the formation of phthalocyanine rings is the predominant cyano-addition reaction, the cross-linked polyimide compositions comply with the general formula:

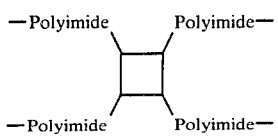
(7)

wherein the central ring is the 29H, 31H-phthalocyanine of formula:

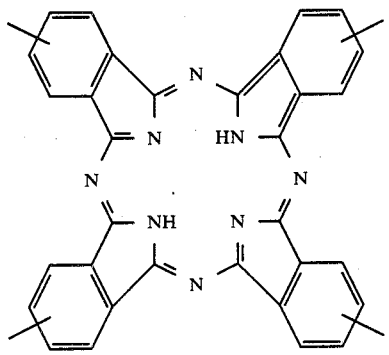
(8)

and where "polyimide" indicates a moiety of the general formula:

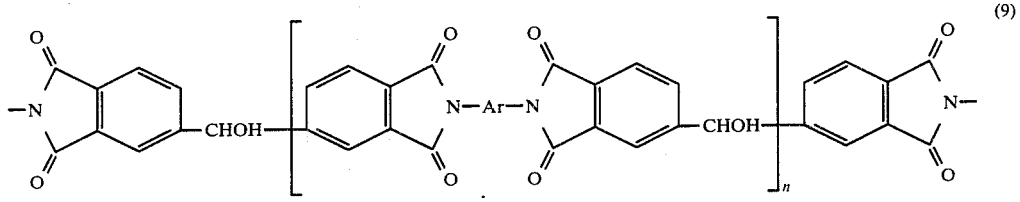
(9)

wherein Ar and n have the same meaning as above.

EXAMPLES

The invention will be described more in detail in relation with the following specific examples wherein the details are given by way of illustration and not limitation. In these examples, polycondensation reactions are performed under stirring and in inert atmosphere so as to avoid oxidation of aromatic amines.

In these examples, the inherent viscosities, when stated, are measured at 30° C. for a concentration of 5 grams of polyimide resin in 1 liter of N-methylpyrrolidone. The molecular weights, when stated, correspond to number average molecular weights calculated from the relative proportions of the initial products.

For sake of simplification in the writing of the names of the chemical products, the mixtures of isomer compounds are designat by a term in the singular as, for example, methyl diester of 3, 3', 4, 4' benzhydrol tetracarboxylic acid.

Two compounds not containing benzhydrol moieties are described in examples A and B. These products, which are 4-benzoyl N-(3,4-dicyano phenyl) phthalimide and N,N'-bis-(3,4-dicyano phenyl)-4,4'-carbonyldiphthalimide, have been prepared for comparison purposes to show that the intramolecular oxidation-reduction phenomenon is attributable to the presence of benzhydrol moieties in polyimide resins, precursors of co-polyphthalocyanine-imides. The model compound of example C,N-(3,4-diacyano phenyl) 4-α-hydroxy benzyl) phthalimide has also been prepared to show this oxidation-reduction reaction.

EXAMPLE A (comparative)

A mixture of 5.044 g of 4-benzoyl phthalic anhydride with 2.863 g of 4-amino phthalonitrile is reacted at 20° C. in 15 cc of N-methylpyrrolidone (NMP). After 2 hours, the solution is heated at 160° C. for 7 hours while distilling the water formed. The product is precipitated in dichloromethane. After drying, the yield is 7.1 g of raw product which is purified by liquid phase chromatography over a silica column. The 4-benzoyl N-(3,4-dicyano phenyl) phthalimide has a melting temperature close to 250° C.

EXAMPLE B (comparative)

In conditions identical to those of example A, 3.222 g of 3, 3', 4, 4' benzophenone tetracarboxylic anhydride are reacted with 2.863 g of 4-amino phthalonitrile in 15 cc of NMP. 5.5 g of N,N'-bis-(3,4-dicyano phenyl) 4,4'-carbonyldiphthalimide are obtained. Their melting point is 260° C.

EXAMPLE C

A mixture of 115 g of 4-benzoyl phthalic anhydride and 300 cc of methanol is heated for 2 hours at 65° C. After cooling, 6 g of palladium on coal and 50 cc of methanol are added. The ketone group is then hydrogenated at room temperature under a hydrogen pressure of 10 bars, for 30 minutes. The catalyst is then removed by filtration and the solvent distilled under vacuum. The yield of 3,4- benzhydrol dicarboxylic acid methyl monoester is 120 g. 57.25 g of said ester and 28.63 g of 4-amino phthalonitrile are heated at 160° C. for 7 hours in 150 cc of NMP. The solution is diluted with 1 liter of dichloromethane, washed several times with water, dried and evaporated. The yield of N-(3,4-dicyano phenyl)-4-(α-hydroxybenzyl) phthalimide is 70 g. The pure product obtained by liquid phase chromatography melts at about 150° C.

EXAMPLE 1

A mixture of 38.83 g of methyl diester of 3, 3', 4, 4'-benzhydrol tetracarboxylic acid with 28.65 g of 4-amino-phthalonitrile and 50 g of N-methyl-pyrrolidone is heated for 2 hours at 160°–170° C. and 0.5 hour at 190° C. The formation of imide is accompanied with the distillation of a mixture of water and methanol (10 g). The cooled solution is poured into 500 ml of water. The product which precipitates is carefully washed with water and dried at 140° C. under vacuum for 20 hours. A light beige solid is obtained with a yield of 92%. Its melting temperature is about 200°–225° C. and its chemical formula, determined by elementary analysis and spectroscopy corresponds to formula (2) wherein radical Ar' is a benzene ring substitued on the carbon atoms in 1,3 and 4 positions.

EXAMPLE 2

A mixture of 36 g of 3, 3', 4, 4'-benzhydrol tetracarboxylic acid with 47.1 g of 4-p-aminophenoxy phthalonitrile in 70 g of N-methylpyrrolidone is heated for 2 hours at 150° C., 2 hours at 165° C. and 1 hour at 185° C. The formation of the imide rings is accompanied with the distillation of 7.2 g of water. At the end of the reaction the solution is poured into 600 ml of water and then treated as in example 1. The diimide, obtained with a yield of 87%, has a melting temperature of 170°–180° C. and corresponds to formula (2) wherein radical Ar' is the 4-(3, 4-dicyano phenoxy) phenyl group.

EXAMPLE 3

A mixture of 32.5 g of dianhydride of 3, 3', 4, 4'-benzhydrol tetracarboxylic acid with 50 g of 4-m-aminobenzoyl phthalonitrile, 100 g of meta-cresol and 20 g of benzene is progressively heated up to 170° C. with azeotropic distillation of the reaction water by means of a Dean and Stark apparatus. At the end of the reaction, i.e. after 4 hours, benzene and the most part of meta-cresol are distilled under reduced pressure. The viscous residue is slowly poured, under strong stirring, into 500 ml of methanol. The precipitate is filtered, washed two times with 100 ml of boiling methanol and dried under vacuum at 130°–140° C. for 24 hours. The resultant diimide, obtained with a yield of 85%, melts at about 200°–207° C. and complies with formula (2) wherein radical Ar' is a 3-(3,4- dicyano benzoyl) phenyl group.

EXAMPLES 4 TO 8

650 g of N-methylpyrrolidone, 466 g of methyl diester of 3, 3', 4, 4'- benzhydrol tetracarboxylic acid and the amount of bis-(4-amino phenyl) methane indicated in table 1. are introduced into a reactor of 2 liters capacity. The solution is stirred and placed in an oil bath heated at 160°–170° C. for 4 hours. Then the amount of 4-amino phthalonitrile indicated in table 1 is added and heating is continued at the same temperature for 3 hours and then at 190°–200° C. for 1 hour. The products are separated as in example 1 by precipitation in water.

The so-prepared polyimide resins have an average molecular weight from 1 000 to 7 000 grams per mole and they comply with the general formula (1) wherein radical Ar is diphenylmethane substituted on 4 and 4' carbon atoms, radical Ar' is benzene, substituted on 1, 3 and 4 carbon atoms and the polycondensation degree n varies from 1 to 19 as indicated in table 1

TABLE I

| Example No | Weight in g of Diamine | A.P.N.[1] | n[2] | $\eta_{inh}$[3] | Molecular Weight[4] |
|---|---|---|---|---|---|
| 4 | 156.62 | 114.5 | 1 | 0.09 | 1060 |
| 5 | 178.44 | 85.9 | 3 | 0.14 | 2030 |
| 6 | 188.26 | 47.3 | 6 | 0.25 | 3500 |
| 7 | 214.13 | 34.4 | 9 | 0.37 | 4950 |
| 8 | 226.03 | 17.2 | 19 | 0.68 | 9820 |

[1]A.P.N.: 4- amino phthalonitrile
[2]n: polycondensation degree
[3]$\eta_{inh}$: inherent viscosity
[4]calculated molecular weight The polyimide resins of examples 4 and 5 have a softening temperature from 200° to 280° C. and may be used by molding. The resins of higher molecular weight of examples 6 to 8 have film-forming properties which are the more enhanced as the polyimide chain is longer. They are thus suitable for the manufacture of protective coatings. Their vitreous transition temperature is about 280° C.

EXAMPLES 9 TO 14

400 g of meta-cresol and 77.67 g of methyl diester of 3,3', 4, 4'-benzhydrol tetracarboxylic acid are introduced into a reactor of 1 liter capacity and, as in example 4, the respective amounts of bis(4-amino phenyl) ether and of 4-amino phthalonitrile indicated in table 2 are reacted therewith in two steps.

At the end of the reaction, the solution, cooled at 50°–60° C., is slowly poured into 3 liters of methanol, under strong stirring by means of a crushing turbine. The polyimide resin which precipitates is washed several times with 0.5 liter of boiling methanol and then dried at 120° C. in vacuum for 24 hours.

By this process, polyimide resins having an average molecular weight from 1 000 to 10 000 grams per mole are obtained.

These resins comply with the general formula (1) wherein radical Ar is diphenyl ether substituted on 4 and 4' carbon atoms, radical Ar' is benzene substituted on 1, 3 and 4 carbon atoms and n is a number from 1 to 19.

TABLE 2

| Example No | Weight in g of Diamine | A.P.N. | n | $\eta_{inh}$ | Molecular Weight |
|---|---|---|---|---|---|
| 9 | 20.02 | 28.63 | 1 | 0.08 | 1060 |
| 10 | 30.37 | 14.33 | 3 | 0.15 | 2040 |
| 11 | 33.37 | 9.54 | 5 | 0.20 | 3020 |
| 12 | 35.04 | 7.16 | 7 | 0.28 | 4000 |
| 13 | 36.04 | 5.73 | 9 | 0.38 | 4970 |
| 14 | 38.05 | 2.87 | 19 | 0.70 | 9850 |

The polyimide resins of examples 9 and 10 have a softening temperature from 215° to 290° C. and can be used by molding. The resins of higher molecular weight of examples 11 to 14 have a vitreous transition temperature close to 280° C. and are more convenient for manufacturing protective coatings.

EXAMPLE 15

A mixture of 64.85 g of dianhydride of 3, 3', 4, 4'-benzhydrol tetracarboxylic acid, 54.07 g of metaphenylenediamine, 99.13 g of bis(4-amino phenyl) methane and 28.63 g of 4-amino phthalonitrile is stirred at room temperature for 4 hours and then heated for 2 hours at 150° C., 2 hours at 170° C. and 1 hour at 190° C. in 1 liter of N-methylpyrrolidone.

The resin, obtained after precipitation in water with a yield of 96%, has a softening temperature of about 220° C.

EXAMPLE 16

This example is given by way of comparison for showing the intramolecular oxidation-reduction phenomenon. Model compounds of examples A and C are subjected to differential thermal analysis with a Mettler thermal analyzer programmed for a temperature increase of 10° C./min.

The thermal analysis curve of 4-benzoyl N-(3,4-dicyano phenyl) phthalimide of example A shows only a melting endotherm at 250° C. The corresponding curve of N-(3,4-dicyano phenyl)-4-hydroxy benzyl phthalimide shows a wide melting endotherm from 100° to 200° C. and an exothermic reaction peak at 315° C.

When these two products are separately heated in inert atmosphere at 300° C. for 1 hour, the compound of example A is not substantially converted, whereas the compound of example C is converted to phthalocyanine. This conversion is detected by the complete disappearance of the infrared absorption bands due to nitrile groups at 2 230 cm$^{-1}$, the appearance of an absorption band of ketone carbonyl at 1 660–1 670 cm$^{-1}$ and the appearance, in the ultraviolet spectrum, of absorption bands characteristic of phthalocyanine rings.

EXAMPLE 17

This example is also given by way of comparison since it concerns the behaviour on heating of N,N'-bis-(3,4-dicyano phenyl)-4,4'-carbonyl diphthalimide prepared in example 13. When this compound is subjected to differential thermal analysis, it shows merely an endothermic transition at 260° C., corresponding to its melting temperature. After thermal treatment for 30 minutes at 300° C., the compound was substantially unconverted and the infrared, ultraviolet and nuclear magnetic resonance spectra wereidentical to those of the starting material.

EXAMPLE 18

The benzhydrol derivative prepared in example 1 is subjected to differential thermal analysis. The obtained curve shows a melting endothermic transition beginning at about 220° C. with a maximum at 250° C. An exothermic reaction peak appears immediately thereafter with a maximum at 280° C.

A sample of 5 g of compound of example 1 is placed in a glass vessel which is dipped into a metal bath heated at 220°–230° C. The product softens at about 190° C. and becomes fluid at the reaction temperature. The liquid quickly takes a green color and its viscosity increases after 2–3 minutes of heating. In less than 10 minutes the resin becomes a dark green solid which does not melt at 300° C.

The infrared spectra of the product during polymerization give an indication on the proportion of the nitrile groups which have reacted, by comparing the respective intensities of the absorption band of these groups at 2 230 cm$^{-1}$. For an initial intensity arbitrarily set at 100, values of 60, 55, 44 and 30 are obtained after respectively 1, 2, 3 and 10 minutes of heating. The resin gelation hence takes place when 60–70% of the phthalonitrile groups are converted to phthalocyanine.

After the setting of the resin, the cyano-addition reactions continue much more slowly in solid phase and a post-baking treatment of about 10 hours at 280° C. is required to obtain the disappearance of the absorption band due to nitrile groups in the infrared spectrum.

When the product of example 1 is directly treated at 300° C. for 1 hour, the infrared band of nitrile groups disappears from the spectrum whereas a ketone carbonyl band is present at 1670 cm$^{-1}$.

The thermogravimetric analysis of the cross-linked resin of copolyphthalocyanine-imide shows that, in inert atmosphere, the weight loss is nil up to 300° C. It is 1% at 400° C. and 10% at 570° C.

EXAMPLE 19

The polyimide resin prepared in example 7 is dissolved in N-methylpyrrolidone in such a proportion as to obtain a 40% concentration of dry material. This solution is used for impregnating a glass fabric E-18 treated with a γ-aminopropyltriethoxysilane textile finishing.

The glass fabric is impregnated on both sides so as to obtain, after evaporation of the solvent, a pre-impregnated fabric containing 35% of resin and 65% of glass fabric. This fabric, dried at 140° C. in a stove with forced ventilation, is then cut up into 16 identical elements of 20×20 cm.

These elements are superposed and placed between the two plates of a hydraulic press heated at 250° C. After 5 minutes of contact, a pressure of 20 bars is applied and the temperature is brought to 300° C. in 20 minutes. The treatment under pressure at 300° C. lasts 2 hours. After cooling under pressure, a stratified material is obtained. It is of dark green color and has a void percentage lower than 1%. The thermogravimetric analysis of this material indicates that, in inert atmosphere, the decomposition of the organic matrix begins at about 500° C. and becomes sufficiently rapid at 550° C. The material does not lose weight after 1 000 hours at 250° C. and loses only 10% of its weight after 1 000 hours at 300° C.

EXAMPLE 20

50 g of the resin of example 13 and 50 g of the resin of example 1 are intimately mixed in a ball breaker. The resultant mixture is placed in a cylindrical mold of 10 cm diameter which is heated at 250° C. under a pressure of 10 bars. After 10 minutes at said temperature, the material is heated for 2 hours at 300° C. By cooling, a homogeneous and dense dark green disk of crosslinked polyimide is obtained. After annealing for 24 hours at 280° C., this molded material has an excellent thermal stability and can be used over a long period at a temperature between 250° and 300° C.

EXAMPLE 21

A 20% by weight solution in meta-cresol of the polyimide composition of example 13 is spread on a copper plate with a filmograph of 150 microns. The solvent is evaporated in a stove with forced ventilation, at 80°, 100°, 120° and 150° C. for 15 minutes at each of said temperatures. The coating is then hardened for 1 hour at 200°, 250°, 280° and 300° C. to obtain a varnish of green colour which strongly sticks to the metal. This varnish has a good flexibility and a high scratch resistance. Its thermoplasticity temperature is higher than 350° C.

What is claimed as the invention is:

1. An aromatic polyimide resin composition, obtained by condensing, at least one aromatic compound (A) of the general formula:

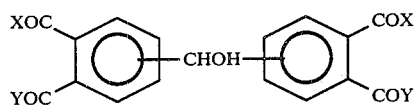

wherein X and Y are independently hydroxy, alkoxy, hydroxyalkoxy, or form together an oxygen atom, and (i) at least one aromatic amino-dinitrile (C) of the general formula:

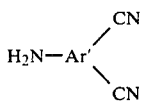

wherein Ar' is a trivalent carbocyclic aromatic radical, the three valencies of which are positioned on separate carbon atoms, the two nitrile groups being in ortho-position with respect to each other; or (ii) a mixture of at least one aromatic amino-dinitrile (C) and at least one aromatic diamine (B) of the general formula:

wherein Ar is a divalent carbocyclic aromatic radical or a pyridine radical, the two valencies of which are positioned on separate carbon atoms and are not in ortho position with respect to each other.

2. A composition according to claim 1, wherein the compounds condensed consist essentially of at least one compound (A) and at least one compound (C) and wherein at least 2 moles of compound (C) are used per mole of compound (A).

3. A composition according to claim 1, wherein 0 to 0.98 mole of compound (B) and 2 to 0.04 moles of compound (C) are condensed per mole of compound (A).

4. A composition according to claim 1, obtained by condensing a 3,3',4,4'-benzhydrol tetra-carboxylic acid or di-anhydride, $C_{1-13}$-alkyl or $C_{1-13}$-hydroxyalkyl tetracarboxylic ester or $C_{1-13}$-alkyl or $C_{1-13}$-hydroxyalkyl dicarboxylic acid-dicarboxylic ester thereof with 4-amino phthalonitrile, 4-p-aminophenoxy phthalonitrile of 4-m-aminobenzoyl phthalonitrile.

5. A composition according to claim 1, obtained by condensing a 3,3',4,4'-benzhydrol tetracarboxylic acid or di-anyhydride, $C_{1-13}$-alkyl or $C_{1-13}$-hydroxyalkyl tetra-carboxylic ester, or $C_{1-13}$-alkyl or $C_{1-13}$-hydroxyalkyl di-carboxylic acid-dicarboxylic ester thereof with bis (4-amino phenyl) methane or bis (4-amino phenyl) ether and then with 4-amino phthalonitrile.

6. A composition according to claim 1, wherein reaction is conducted at a temperature from about 100° to 200° C.

7. A composition according to claim 1, wherein reaction is discontinued before substantial gelation of the resin.

8. A composition according to claim 1, wherein (C) supplies 0.9 to 1.1 primary amino groups per each ortho-difunctional group in (A).

9. A composition according to claim 1 wherein compound (A) is condensed with said mixture of compound (B) and (C).

10. A composition according to claim 9, wherein (B) and (C) supply 0.9 to 1.1 primary amino groups per each ortho-difunctional group in (A).

11. A composition according to claim 1, wherein (C) supply 0.98 to 1.02 primary amino groups per each ortho-difunctional group in (A).

12. A composition according to claim 9, wherein (B) and (C) supply 0.98 to 1.02 primary amino groups per each ortho-difunctional group in (A).

13. A composition according to claim 9, obtained by
(a) condensing at least one diamine (B) with an excess amount of at least one compound (A) with respect to the stoichiometrical proportion of 1 ortho-difunctional group of said compound (A) per primary amine group of said diamine (B), resulting in the formation of an oligomer (D), containing imide groups and free ortho-difunctional groups and having a number average molecular weight ranging from 800 to 25,000; and
(b) reacting said oligomer (D) with at least one amino dinitrile (C), used in a sufficient proportion to obtain a total number of primary amine groups of said compounds (B) and (C) amounting to 0.9-1.1 times the number of ortho-difunctional groups of said compound (A).

14. A composition according to claim 1, wherein reaction is condcted at a temperature of about 80°-300° C.

15. A composition according to claim 9, wherein Ar is a 5-7 atom ring, containing at least one oxygen, sulfur or nitrogen atom.

16. A composition according to claim 15, wherein Ar is a nitrogen-containing 5-7 atom ring.

17. A process for the production of a polyimide resin composition comprising condensing at least one aromatic compound (A) of the formula:

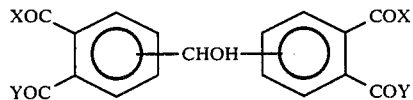

wherein X and Y are independently hydroxy, alkoxy, hydroxyalkoxy, or form together an oxygen atom, and at least one aromatic amino-dinitrile compound (C) of the general formula:

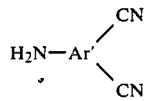

wherein Ar' is a trivalent carbocyclic aromatic radical, the three valencies of which are positioned on separate carbon atoms, the two nitrile groups being in ortho-position with respect to each other; or a mixture of at least one aromatic amino-dinitrile (C) and at least one aromatic diamine compound (B) of the general formula:

wherein Ar is a divalent carbocyclic aromatic radical or a pyridine radical, the two valencies of which are positioned on separate carbon atoms and are not in ortho-position with respect to each other.

18. The phthalo cyanine ring-containing, cross-linked product obtained by heating a composition of claim 1.

19. The phthalo cyanine ring-containing, cross-linked product obtained by heating a composition of claim 8.

20. The phthalo cyanine ring-containing, cross-linked product obtained by heating a composition of claim 10.

* * * * *